US012797628B2

(12) United States Patent
Suehara et al.

(10) Patent No.: US 12,797,628 B2
(45) Date of Patent: Nov. 17, 2026

(54) TREATMENT APPARATUS AND TREATMENT METHOD

(71) Applicant: TERUMO KABUSHIKI KAISHA, Tokyo (JP)

(72) Inventors: Satoru Suehara, Kaisei-machi (JP); Mayu Hata, Yokohama (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 1072 days.

(21) Appl. No.: 17/945,286

(22) Filed: Sep. 15, 2022

(65) Prior Publication Data

US 2023/0021096 A1 Jan. 19, 2023

Related U.S. Application Data

(63) Continuation of application No. PCT/JP2021/009429, filed on Mar. 10, 2021.

(30) Foreign Application Priority Data

Mar. 30, 2020 (JP) ................................ 2020-060402

(51) Int. Cl.
*A61N 5/06* (2006.01)

(52) U.S. Cl.
CPC ........ *A61N 5/06* (2013.01); *A61N 2005/0611* (2013.01); *A61N 2005/063* (2013.01)

(58) Field of Classification Search
CPC .......... A61N 5/06–0601; A61N 5/0603; A61N 2005/0602; A61N 2005/0604–0612
See application file for complete search history.

(56) References Cited

U.S. PATENT DOCUMENTS 5,871,521 A * 2/1999 Kaneda ................ A61N 5/0601 606/14
5,947,958 A 9/1999 Woodard et al.
(Continued)

FOREIGN PATENT DOCUMENTS

JP 2007528754 A 10/2007
KR 101924492 B1 * 12/2018 ............ A61B 18/22
WO 2020138138 A1 7/2020

OTHER PUBLICATIONS

International Search Report (PCT/ISA/210) with translation and Written Opinion (PCT/ISA/237) mailed on May 11, 2021, by the Japanese Patent Office as the International Searching Authority for International Application No. PCT/JP2021/009429. (9 pages).

*Primary Examiner* — Thaddeus B Cox
(74) *Attorney, Agent, or Firm* — .Buchanan Ingersoll & Rooney PC

(57) ABSTRACT

A treatment apparatus and a treatment method capable of effectively treating cancer in a range including at least a part of a cervix. A treatment apparatus is configured to irradiate an antibody-photosensitive substance accumulated in a tumor cell with excitation light, and includes: a tubular device including an elongated tubular member; and an irradiation device configured to be inserted into the tubular member. The irradiation device includes a main shaft including a distal portion and a proximal portion, a disk portion disposed on a distal side of the main shaft, a distal shaft protruding from the disk portion toward the distal side, and an irradiation unit disposed on the distal shaft and configured to emit the excitation light.

20 Claims, 7 Drawing Sheets

(56) References Cited

U.S. PATENT DOCUMENTS

| | | | | |
|---|---|---|---|---|
| 2001/0055462 | A1* | 12/2001 | Seibel | A61B 1/00048 385/33 |
| 2005/0128742 | A1 | 6/2005 | Chen et al. | |
| 2008/0065003 | A1 | 3/2008 | Neuberger et al. | |
| 2008/0249517 | A1* | 10/2008 | Svanberg | A61N 5/0601 606/15 |
| 2009/0198173 | A1* | 8/2009 | Samuel | A61N 5/062 607/93 |
| 2018/0113246 | A1 | 4/2018 | Rose et al. | |
| 2019/0290360 | A1* | 9/2019 | Goodrich | A61B 18/24 |
| 2020/0289840 | A1* | 9/2020 | Vermandel | A61N 5/062 |

* cited by examiner

TREATMENT APPARATUS AND TREATMENT METHOD

CROSS-REFERENCES TO RELATED APPLICATIONS

This application is a continuation of International Application No. PCT/JP2021/009429 filed on Mar. 10, 2021, which claims priority to Japanese Application No. 2020-060402 filed on Mar. 30, 2020, the entire content of both of which is incorporated herein by reference.

TECHNOLOGICAL FIELD

The present disclosure generally relates to a treatment apparatus and a treatment method for cervical cancer.

BACKGROUND DISCUSSION

The number of patients with cervical cancer has an increasing tendency, and in particular, the number of young female patients in their 20s and 30s is increasing. In current treatment for cervical cancer, treatment can include removing an entire uterus from an early stage (stage I). However, for young patients, local treatment is required to conserve the uterus in order to maintain fertility. Further, in advanced stages (stage III and subsequent stages), when cancer has spread to surrounding tissues, it is difficult to remove by surgery, and thus treatment can include combining radiation therapy and chemotherapy. However, a five-year survival rate is as low as 50% in stage III and 20% in stage IV, and more effective treatment is required. As the local treatment for cancer, a treatment method using a photoreactive substance is known (for example, see United States Patent Application Publication No. 2018/0113246). In particular, a treatment method using an antibody-photosensitive substance (hydrophilic phthalocyanine) can specifically destroy target cells without destroying non-target cells such as normal cells by irradiating the antibody-photosensitive substance accumulated in a tumor with excitation light (for example, near-infrared rays), and is expected to achieve a relatively high treatment effect while minimizing side effects.

Meanwhile, in order to achieve a high treatment effect by the antibody-photosensitive substance, the antibody-photosensitive substance adsorbed to the tumor is required to be reliably irradiated with the near-infrared rays. However, the near-infrared rays have a relatively small penetration depth, and thus can be hardly emitted from a body surface to a solid cancer in a noninvasive manner. This leads to a requirement of a method for reliably irradiating a tumor in a body with light while reducing invasiveness as much as possible. In the case of cervical cancer, cancer often spreads over a wide range of a cervical canal, and a method for irradiating cancer in a wide range with light from as close as possible is required.

SUMMARY

A treatment apparatus and a treatment method capable of effectively treating cancer in a range including at least a part of a cervix.

A treatment apparatus is disclosed, which is configured to irradiate an antibody-photosensitive substance accumulated in a tumor cell of cervical cancer with excitation light. The treatment apparatus includes: a tubular device including an elongated tubular member; and an irradiation device configured to be inserted into the tubular member. The irradiation device includes a main shaft including a distal portion and a proximal portion, a disk portion disposed on a distal side of the main shaft, a distal shaft protruding from the disk portion toward the distal side, and an irradiation unit disposed on the distal shaft and configured to emit the excitation light.

According to the treatment apparatus described above, the excitation light can be effectively emitted to the antibody-photosensitive substance accumulated in the tumor cell in a wide range including a cervix in a state in which the distal shaft is inserted into a cervical canal and the tubular member is inserted into the vicinity of a vaginal vault. Therefore, this treatment apparatus can improve a treatment effect of cancer in a range including at least a part of the cervix.

The distal shaft may be configured to emit the excitation light in a direction substantially perpendicular to an axial center of the distal shaft, and the disk portion may be configured to emit the excitation light in a substantially distal direction. Accordingly, the excitation light can be emitted to the tumor cell of the cervix from both the distal shaft and the disk portion, and thus the treatment effect can be improved.

The tubular member may include a second irradiation unit configured to emit the excitation light in a direction substantially perpendicular to an axial center direction of the tubular member and/or in a substantially distal direction. Accordingly, the excitation light can be directly emitted from the second irradiation unit provided in the tubular member to the tumor cell in the vaginal vault, which is difficult for light to reach, and thus the treatment effect can be improved.

A distal portion of the tubular member may be configured to be deformed. Accordingly, the distal portion can be deformed along the vaginal vault to be disposed in the vicinity of the vaginal vault. Therefore, the excitation light can be effectively emitted to the vicinity of the vaginal vault, which is difficult for light to reach, and the treatment effect can be improved.

The treatment apparatus may further include a fixing portion configured to fix the irradiation device to the tubular device. Accordingly, the irradiation device and the tubular member can be operated as one, and thus operability can be improved. Since the irradiation device can be maintained at an appropriate position with respect to the tubular member, the excitation light emitted from the irradiation device can be appropriately propagated to the tubular member. Therefore, the excitation light emitted from the distal shaft, the disk portion, and the tubular member can be appropriately emitted to the antibody-photosensitive substance.

The fixing portion may be a balloon that is disposed on the disk portion and configured to be inflated by inflowing a fluid in the balloon. Accordingly, by inflating the balloon inside the tubular member, the irradiation device can be rather easily and reliably fixed to the tubular member.

The fixing portion may be a balloon that is disposed on the tubular member and configured to be inflated by inflowing a fluid in the balloon. Accordingly, by inflating the balloon, the irradiation device can be rather easily and reliably fixed to the tubular member.

An axial center of the disk portion may be inclined with respect to an axial center of the main shaft, which facilitates disposing the disk portion in accordance with an inclination of a uterine vagina with respect to a vagina. Therefore, the excitation light emitted from the disk portion can be appropriately emitted to the antibody-photosensitive substance.

The treatment apparatus may further include a detection unit configured to detect fluorescence emitted by the antibody-photosensitive substance. Accordingly, a degree of destruction of the tumor cell due to emission of the excitation light can be checked by a change in the fluorescence detected by the detection unit.

A treatment method is disclosed, for example, for treating cervical cancer. The treatment method includes: intravenously administering an antibody-photosensitive substance; inserting a tubular member into a living body, for example, a vagina 12 hours to 36 hours after the intravenous administration; inserting an irradiation device into the tubular member, the irradiation device including a disk portion configured to be disposed inside the tubular member, a distal shaft protruding from the disk portion toward a distal side, and an irradiation unit configured to emit excitation light of the antibody-photosensitive substance; inserting the distal shaft into a body lumen, for example, a cervical canal while visually checking the distal shaft; and causing the irradiation unit to emit light and emitting the excitation light from the disk portion, the distal shaft, and the tubular member to a surrounding tissue.

According to the treatment method described above, the distal shaft can be inserted from an external uterine ostium into the cervical canal, and the tubular member can be inserted up to the vaginal vault or near the vaginal vault, and thus by emitting the excitation light of the antibody-photosensitive substance from the distal shaft, the disk portion, and the tubular member, the excitation light can be effectively emitted to the antibody-photosensitive substance accumulated in the tumor cell in a range including at least a part of the cervix. Therefore, this treatment method can improve the treatment effect of cancer in a range including at least a part of the cervix.

The treatment method may further include fixing a position of the irradiation device to the tubular member. Accordingly, the irradiation device and the tubular member can be operated as one, and thus the operability is improved. Since the irradiation device can be maintained at an appropriate position with respect to the tubular member, light emitted from the irradiation device can be appropriately propagated to the tubular member. Therefore, the excitation light emitted from the distal shaft, the disk portion, and the tubular member can be appropriately emitted to the antibody-photosensitive substance.

The treatment method may further include detecting fluorescence emitted by the antibody-photosensitive substance and checking an intensity of the fluorescence. Accordingly, in this treatment method, the degree of the destruction of the tumor cell due to the emission of the excitation light can be checked by detecting the fluorescence.

The checking of the intensity of the fluorescence may be performed in parallel with the emitting of the excitation light. Accordingly, in this treatment method, a tumor can be treated while detecting the fluorescence to check the degree of the destruction of the tumor cell due to the emission of the excitation light, and the treatment effect can be improved.

The checking of the intensity of the fluorescence may be performed after the emitting of the excitation light. Accordingly, in this treatment method, a result of the destruction of the tumor cell due to the emission of the excitation light can be accurately checked by detecting the fluorescence.

Another treatment method is disclosed, which includes: intravenously administering an antibody-photosensitive substance; inserting a tubular member into a living body after the intravenous administration; inserting an irradiation device into the tubular member, the irradiation device including a disk portion configured to be disposed inside the tubular member, a distal shaft protruding from the disk portion toward a distal side, and an irradiation unit configured to emit excitation light of the antibody-photosensitive substance; inserting the distal shaft into a body lumen; and causing the irradiation unit to emit light and emitting the excitation light from the disk portion, the distal shaft, and the tubular member to a surrounding tissue.

BRIEF DESCRIPTION OF THE DRAWINGS

FIGS. 2A and 2B are schematic views illustrating a vagina and a uterus, in which FIG. 2A illustrates a state of a patient viewed from front, and FIG. 2B illustrates a state of the patient viewed from a left side.

FIGS. 5A and 5B are plan views illustrating distal shafts according to modifications, in which FIG. 5A illustrates a first modification, and FIG. 5B illustrates a second modification.

FIGS. 7A to 7C are cross-sectional views illustrating disk portions according to modifications, in which FIG. 7A illustrates a fourth modification, FIG. 7B illustrates a fifth modification, and FIG. 7C illustrates a sixth modification.

FIGS. 8A and 8B are cross-sectional views illustrating disk portions according to modifications, in which FIG. 8A illustrates a seventh modification, and FIG. 8B illustrates an eighth modification.

FIGS. 9A and 9B are cross-sectional views illustrating disk portions according to modifications, in which FIG. 9A illustrates a ninth modification, and FIG. 9B illustrates a 10th modification.

FIGS. 10A to 10C are plan views illustrating irradiation units according to modifications, in which FIG. 10A illustrates the present embodiment, FIG. 10B illustrates an 11th modification, and FIG. 10C illustrates a 12th modification.

FIGS. 11A to 11C are plan views illustrating tubular members according to modifications, in which FIG. 11A illustrates a 13th modification, FIG. 11B illustrates a 14th modification, and FIG. 11C illustrates a 15th modification.

DETAILED DESCRIPTION

Figure 1:
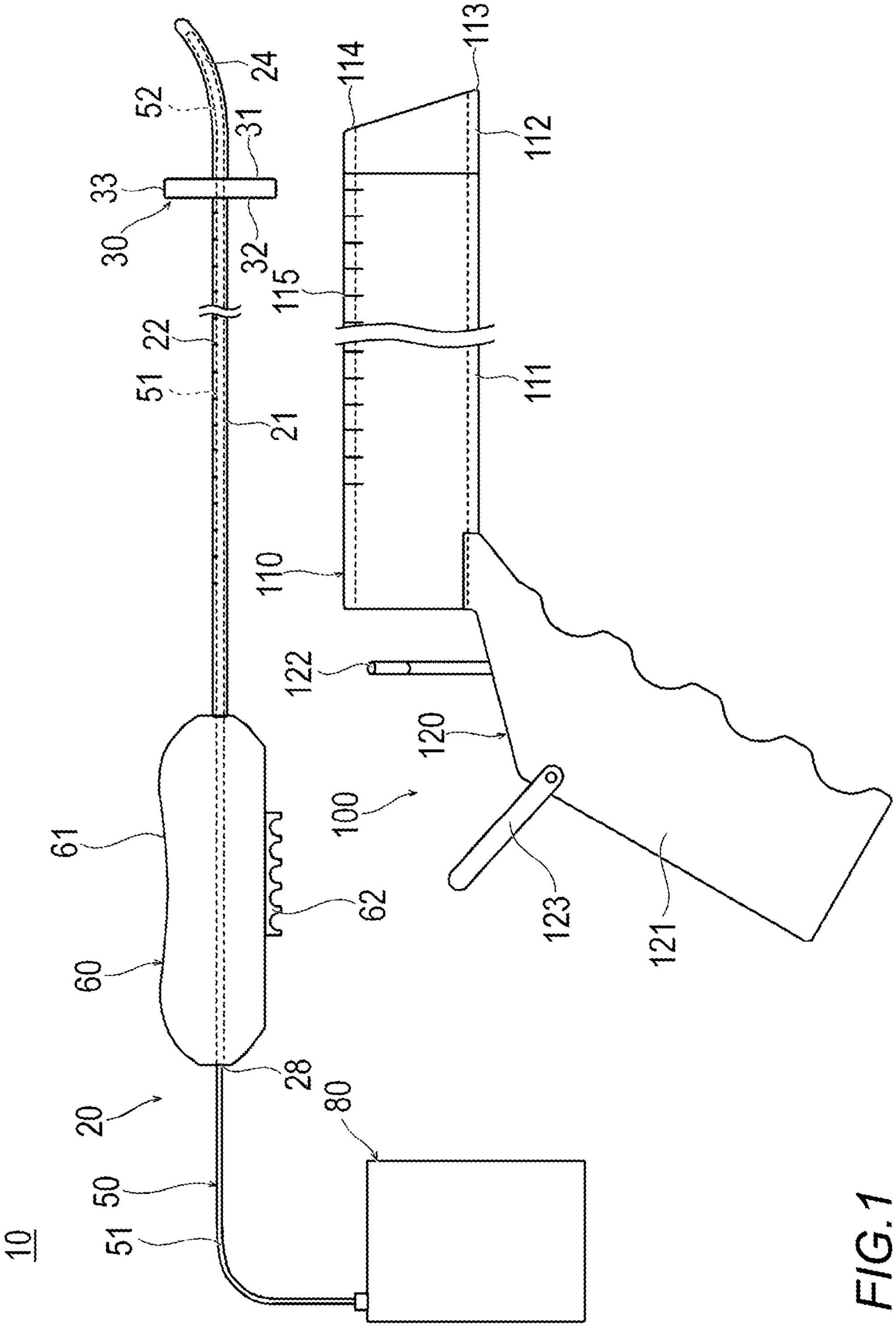
FIG. 1 is a plan view illustrating a treatment apparatus according to an embodiment.
Figure 2A:
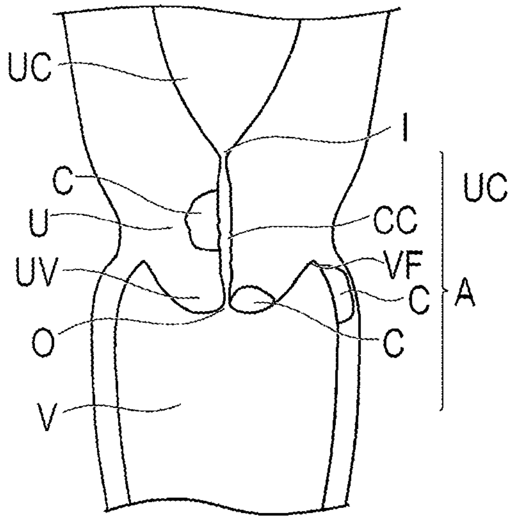
Figure 2B:
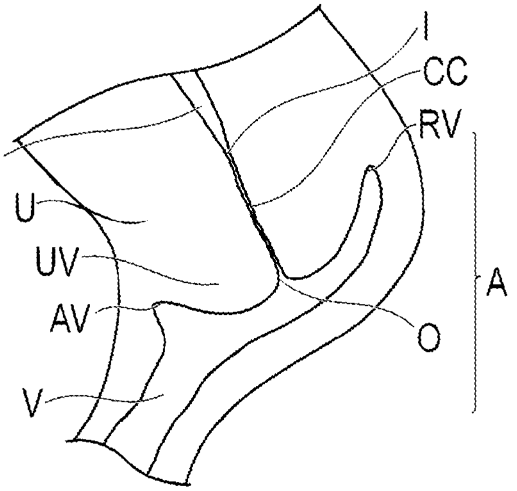

Set forth below with reference to the accompanying drawings is a detailed description of embodiments of a treatment apparatus and a treatment method for cervical cancer. Note that since embodiments described below are preferred specific examples of the present disclosure, although various technically preferable limitations are given, the scope of the present disclosure is not limited to the embodiments unless otherwise specified in the following descriptions. For convenience of explanation, dimensions in the drawings may be exaggerated and may be different from actual dimensions. In the present specification and the drawings, components having substantially the same functional configuration are designated by the same reference numerals, and a duplicate description of the components having substantially the same functional configuration will be omitted. In the present specification, a side of a device to be inserted into a body lumen is referred to as a "distal side", and a side to be operated is referred to as a "proximal side".

A treatment apparatus 10 according to the present embodiment is used for a treatment method for cervical cancer. The treatment apparatus 10 and the treatment method can also be used to simultaneously treat both cervical cancer and vaginal cancer. The treatment method can be used for photoimmunotherapy in which an antibody-photosensitive substance accumulated in cell membranes of target cells is irradiated with near-infrared rays, which serve as excitation light of the antibody-photosensitive substance, to destroy the target cells. The target cells are tumor cells such as cancer cells. In this treatment method, the antibody-photosensitive substance, which is obtained by binding an antibody specifically accumulated only in a specific antigen on surfaces of the tumor cells and a photosensitive substance paired with the antibody, is used as a drug. The antibody is not particularly limited, and may be, for example, panitumbab, trastuzumab, HuJ591, pertuzumab, lapatinib, palbociclib, and olaparib. The photosensitive substance can be, for example, hydrophilic phthalocyanine which is a substance that reacts with near-infrared rays having a wavelength of about 700 nm (IR700), but is not limited to hydrophilic phthalocyanine. When IR700 receives near-infrared rays having a wavelength of about 660 nm to 740 nm, a ligand of a functional group that secures water solubility is broken, causing a structural change of the IR700 from water-soluble to hydrophobic. Due to this structural change, membrane protein is extracted, holes are opened in the cell membranes, and water enters the cells, so that the cancer cells can be ruptured and destroyed. IR700 can be excited by receiving the near-infrared rays, and emits fluorescence having a wavelength different from an excitation wavelength. For example, IR700 emits fluorescence having a wavelength of 704 nm when excited by receiving near-infrared rays having a wavelength of 689 nm. A structural change of the IR700 occurs while emitting the fluorescence by a photoreaction, and IR700 also stops emitting the fluorescence when the tumor cells are destroyed and the role as a drug is finished.

The treatment apparatus 10 illustrated in FIG. 1 can treat, with one device, cervical cancer and vaginal cancer in a relatively wide range A, which is illustrated in FIGS. 2A, 2B, 12, and 13, and can include a cervix U, an external uterine ostium O, a uterine vagina UV around the external uterine ostium O, a vaginal vault VF, and a site or location near the vaginal vault VF on a vaginal introitus side relative to the vaginal vault VF of a vagina V. The treatment apparatus 10 can emit the excitation light to the antibody-photosensitive substance accumulated in tumor cells C in a relatively wide range from the cervix U to the vagina V.

A uterus is positioned behind the vagina V, an upper portion of the uterus is connected to left and right fallopian tubes, and the external uterine ostium O at a lower portion of the uterus is connected to the vagina V. The uterus is roughly divided into a uterine corpus and the cervix U, and the cervix U includes a cervical canal CC connected to the external uterine ostium O. The vagina V includes the vaginal vault VF that expands around the external uterine ostium O. The vaginal vault VF is deeper at a posterior vaginal vault RV positioned in a posterior part of the vagina V than at an anterior vaginal vault AV positioned at an anterior part of the vagina V.

First, the treatment apparatus 10 according to the present embodiment will be described.

Figure 3:
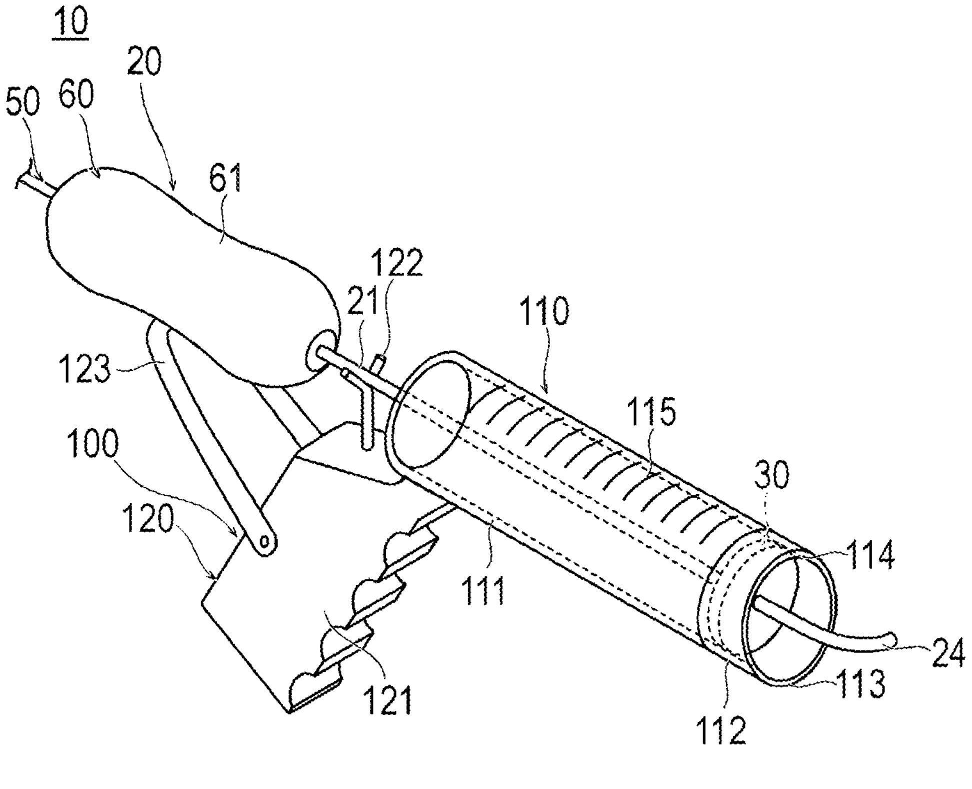
FIG. 3 is a perspective view illustrating the treatment apparatus according to the embodiment.

As illustrated in FIGS. 1 and 3, the treatment apparatus 10 can include an irradiation device 20 having a function of emitting near-infrared rays, and a tubular device 100 including a tubular member 110.

The irradiation device 20 can include a main shaft 21 including a distal portion and a proximal portion, an elongated irradiation unit 50 that emits light, a distal shaft 24 that accommodates the irradiation unit 50, a disk portion 30 provided at the distal portion of the main shaft 21, and a first operation portion 60 connected to a proximal portion of the irradiation device 20. The treatment apparatus 10 can be used by being connected to a light output device 80.

The main shaft 21 can be a tubular body that supports the disk portion 30. The main shaft 21 accommodates a part of the elongated irradiation unit 50. The main shaft 21 can be a circular tube extending linearly, but may be bent or may not be a circular tube. The proximal portion of the main shaft 21 is fixed to the first operation portion 60. The distal portion of the main shaft 21 is fixed to a proximal portion of the disk portion 30. Scale marks 22 arranged in an axial center direction are attached to an outer peripheral surface of the main shaft 21. The scale marks 22 can be used to check a depth of insertion of the main shaft 21 into the tubular device 100 or a living body such as the vagina V.

The main shaft 21 preferably has a certain degree of rigidity such that an operator can hold the first operation portion 60 to push the main shaft 21 to a desired position. A constituent material for the main shaft 21 is not particularly limited, and can include: a metal represented by stainless steel, aluminum, titanium alloys, tin, magnesium alloys, or the like; a resin represented by polyetheretherketone (PEEK), polyamide, acrylonitrile butadiene styrene (ABS), polycarbonate, polyacetal, polyimide; or the like. A length of the main shaft 21 in the axial center direction is not particularly limited, and can be, for example, 100 mm to 400 mm.

The distal shaft 24 can be a tubular member capable of accommodating the irradiation unit 50 in the tubular member of the distal shaft 24, and is capable of transmitting light outward from the irradiation unit 50. A part of the distal shaft 24 is disposed inside the disk portion 30. The distal shaft 24 extends toward the distal side relative to the disk portion 30. The distal shaft 24 is a portion to be inserted from the external uterine ostium O into the cervical canal CC in order to emit light from an inside of the cervical canal CC to the cervix U (see FIG. 12). A proximal portion of the distal shaft 24 extends toward the proximal side relative to the main shaft 21 and the first operation portion 60. An irradiation lumen 25 in which the irradiation unit 50 can be disposed is continuously formed inside the main shaft 21 and the distal shaft 24. The irradiation lumen 25 is closed at a most distal end of the distal shaft 24, and is opened at a most proximal end of the main shaft 21. An insertion port 28 for receiving the irradiation unit 50 into the irradiation lumen 25 is disposed on a proximal side of the main shaft 21. The distal shaft 24 preferably has a function of diffusing light. Therefore, similarly to the disk portion 30 which will be described in detail later, the distal shaft 24 may contain scatterers in at least a part of a constituent material, may have multiple irregularities formed on an inner surface or an outer surface of the distal shaft 24, or may have a multi-layer structure in which materials having different refractive indexes are joined by a surface on which multiple irregularities are formed.

The distal shaft 24 is preferably curved to facilitate passing the distal shaft 24 through the cervical canal CC which is inclined with respect to the vagina V, but may also be formed linearly without being curved. The distal shaft 24 can be rigid, substantially rigid, or flexible. The distal shaft 24 can be formed of a transparent or translucent material capable of transmitting light having a wavelength emitted by the irradiation unit 50 accommodated in the distal shaft 24. The constituent material for the distal shaft 24 is not particularly limited, and can include: a resin represented by polymethyl methacrylate, polyethylene terephthalate, polycarbonate, polytetrafluoroethylene, or the like; glass; or the like. It is more preferable that the material for the distal shaft 24 has elasticity and has a physical property allowing the distal shaft 24 to be deformed while being bent along the cervical canal CC after being inserted into the cervical canal CC. Accordingly, it is possible to cope with individual differences in a shape of the cervical canal CC, and it is possible to reduce a burden on an inner surface of the cervical canal CC and to further improve adhesion to the inner surface of the cervical canal CC. An outer diameter of the distal shaft 24 is not particularly limited, and can be, for example, 0.5 mm to 6 mm. A length of the distal shaft 24 in the axial center direction is not particularly limited, and can be, for example, 10 mm to 50 mm.

Figure 5A:
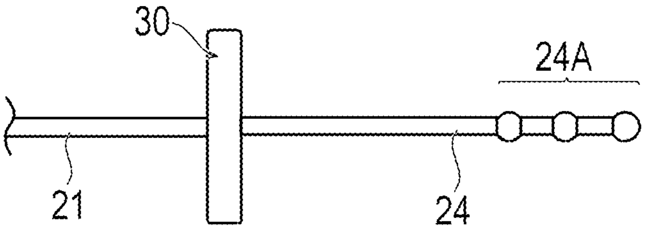

A shape of the distal shaft 24 is not particularly limited. For example, as in a first modification illustrated in FIG. 5A, the distal shaft 24 may include irregular structures 24A arranged in the axial center direction. Accordingly, when inserting the distal shaft 24 from the external uterine ostium O into the cervical canal CC, the operator can relatively easily grasp a length of insertion of the distal shaft 24 into the cervical canal CC by visually checking the irregular structure 24A. When inserting the irregular structure 24A from the external uterine ostium O into the cervical canal CC, the operator can relatively easily grasp the length of insertion of the distal shaft 24 into the cervical canal CC based on a change in sensation received by a hand holding the first operation portion 60. As a structure that facilitates visual check, the distal shaft 24 may have a line, a notch, or the like serving as a scale. The distal shaft 24 may have physical properties that change along the axial center direction such that the sensation received by the hand of the operator changes when the operator inserts the distal shaft 24 from the external uterine ostium O into the cervical canal CC. For example, the distal shaft 24 may have a decrease in rigidity toward a distal direction, or may have high-rigidity portions and low-rigidity portions alternately arranged.

Figure 5B:
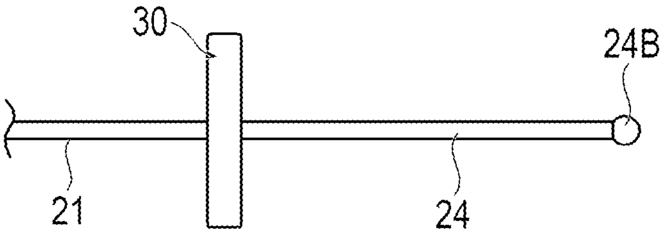

As in a second modification illustrated in FIG. 5B, the distal shaft 24 may include a distal portion provided with one large-diameter portion 24B having a large outer diameter. Accordingly, after inserting the distal shaft 24 from the external uterine ostium O into the cervical canal CC, the operator can relatively easily grasp, based on the change in the sensation received by the hand holding the first operation portion 60, that the large-diameter portion 24B crosses an internal cervical ostium I and reaches a uterine cavity UC. For example, the operator can retract the first operation portion 60 and bring the large-diameter portion 24B into contact with the internal cervical ostium I after the large-diameter portion 24B crossed the internal cervical ostium I. Therefore, the distal shaft 24 including the large-diameter portion 24B is effective when it is desired to accurately position the distal portion of the distal shaft 24 with respect to the internal cervical ostium I, or when it is desired to reliably pass the distal portion of the distal shaft 24 through the internal cervical ostium I. A position of the large-diameter portion 24B is not limited to a most distal end of the distal shaft 24.

Figure 6:
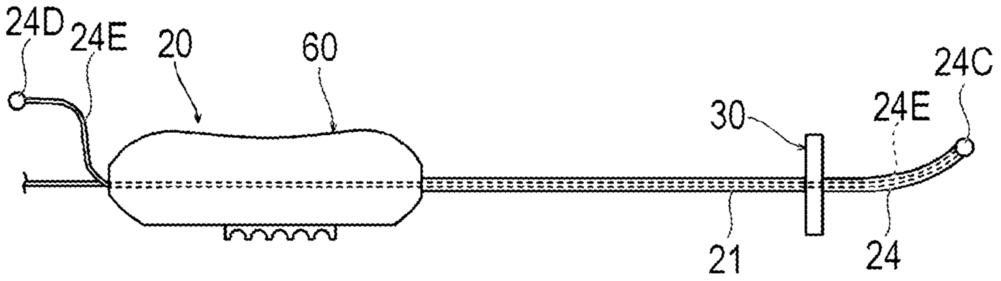
FIG. 6 is a plan view illustrating a third modification.

As in a third modification illustrated in FIG. 6, the distal shaft 24 may include a distal portion provided with a bag-shaped first balloon 24C that is flexibly deformable. The first balloon 24C communicates with a bag-shaped second balloon 24D disposed on the first operation portion 60 by a tube 24E. A fluid is sealed in the first balloon 24C, the second balloon 24D, and the tube 24E. Accordingly, when the distal shaft 24 enters the cervical canal CC from the external uterine ostium O, the first balloon 24C is compressed, the fluid inside the first balloon 24C moves toward the second balloon 24D, and the second balloon 24D is inflated. Accordingly, the operator can relatively easily grasp, by viewing the second balloon 24D, that the distal shaft 24 including the first balloon 24C enters the cervical canal CC. When the first balloon 24C crosses the internal cervical ostium I, the first balloon 24C is inflated due to a restoring force, the fluid inside the second balloon 24D moves toward the first balloon 24C, and the second balloon 24D becomes smaller. Accordingly, the operator can relatively easily grasp, by viewing the second balloon 24D, that the distal shaft 24 including the first balloon 24C crosses the internal cervical ostium I.

The operator may insert the distal shaft 24 from the external uterine ostium O into the cervical canal CC in a state in which the irradiation unit 50 disposed inside the distal shaft 24 is caused to emit light. Light emitted from a portion of the distal shaft 24 inserted into the cervical canal CC is not visible to the operator. Therefore, the operator can relatively easily visually grasp the length of insertion of the distal shaft 24 into the cervical canal CC. In this case, even if the distal shaft 24 is not provided with the irregular structure 24A or the large-diameter portion 24B, the operator can visually grasp the length of insertion of the distal shaft 24 into the cervical canal CC.

Figure 4:
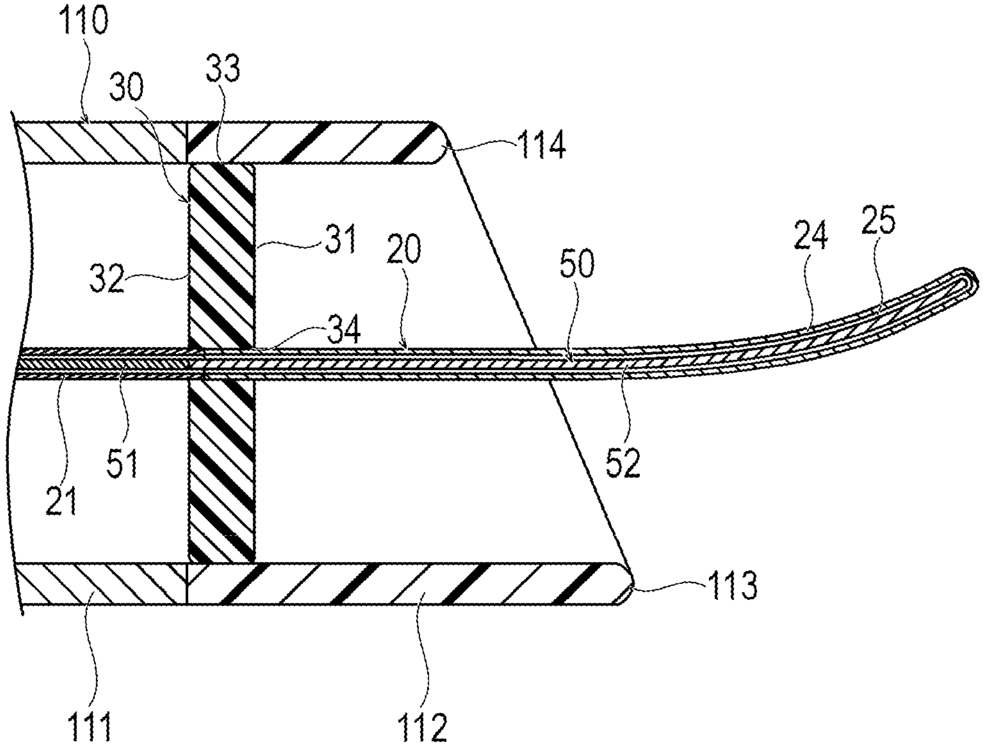
FIG. 4 is a cross-sectional view illustrating a distal portion of the treatment apparatus according to the embodiment.
Figure 12:
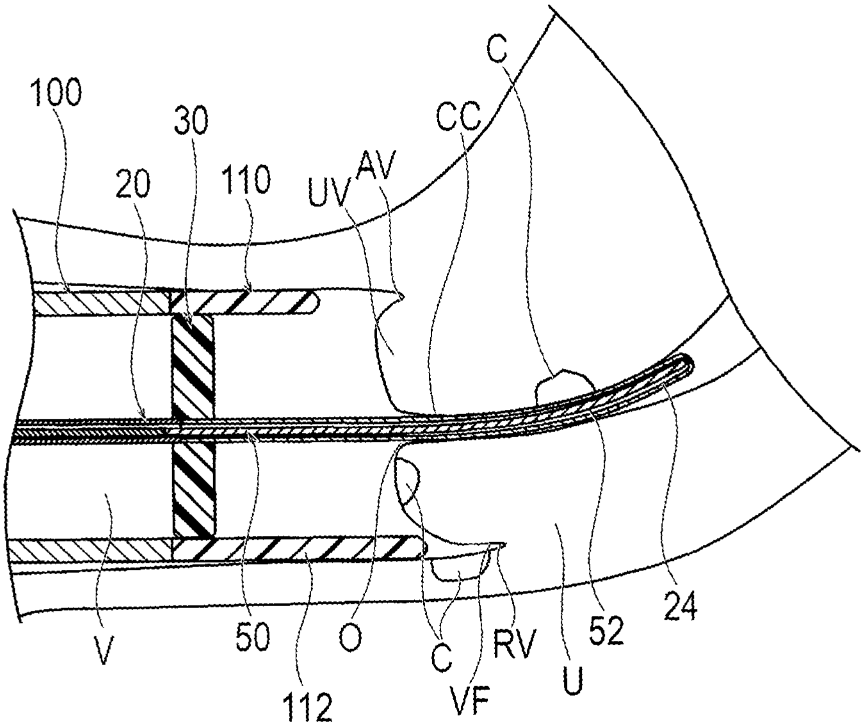
FIG. 12 is a schematic view illustrating a state in which the distal shaft of the treatment apparatus according to the embodiment is inserted into a cervical canal.
Figure 13:
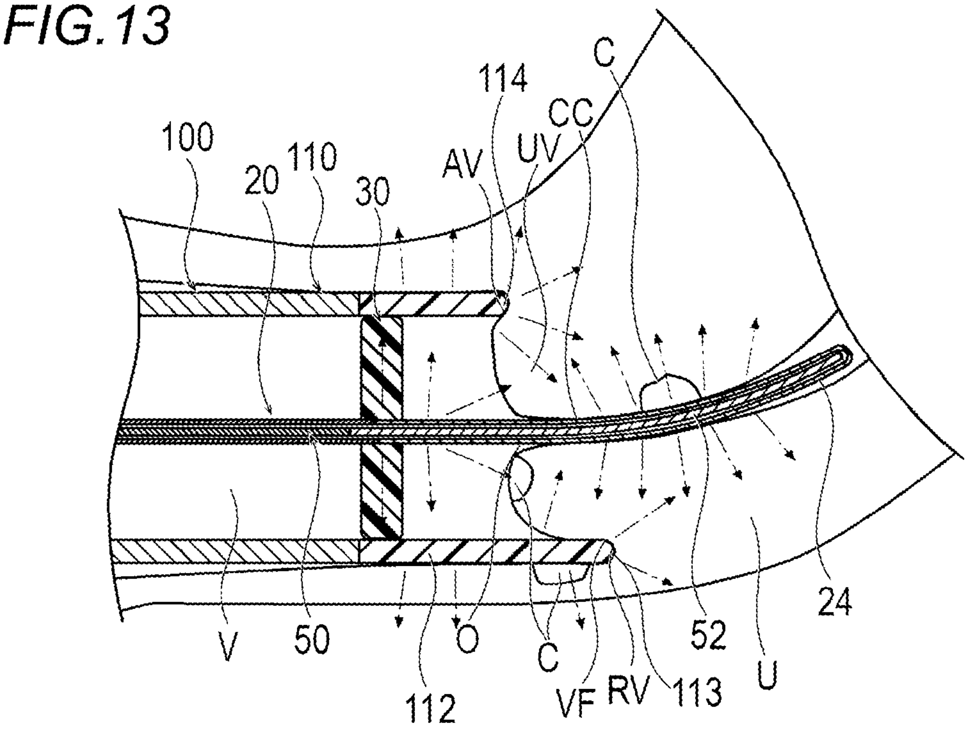
FIG. 13 is a schematic view illustrating a state in which near-infrared rays are emitted from the treatment apparatus according to the embodiment to tumor cells.

As illustrated in FIGS. 4, 12, and 13, the disk portion 30 is a member that is disposed on a proximal side of the distal shaft 24 to be inserted into the cervical canal CC, and is capable of being inserted into the vagina V and emitting light in a wide range of the vagina V. The disk portion 30 is disposed inside a portion on the proximal side relative to a most distal end of the tubular member 110. The disk portion 30 can transmit outward light emitted from the irradiation unit 50 disposed in the irradiation lumen 25 that passes through an inside of the disk portion 30. Therefore, the disk portion 30 is formed of a transparent or translucent material capable of transmitting light having a wavelength emitted by the irradiation unit 50.

As illustrated in FIGS. 1, 3, and 4, the disk portion 30 is a disk-shaped member fixed to the distal portion of the main shaft 21. The disk portion 30 may be movable relative to the main shaft 21 along an axial center of the main shaft 21. The disk portion 30 can include a distal surface 31, a proximal surface 32, an outer surface 33, and a through hole 34. The distal surface 31 and the proximal surface 32 are substantially perpendicular to the axial center of the main shaft 21. The through hole 34 is positioned substantially at centers of the distal surface 31 and the proximal surface 32, and penetrates between the distal surface 31 and the proximal surface 32. The main shaft 21 is inserted into the through hole 34 from the proximal side and fixed to the through hole 34, and the distal shaft 24 is inserted into the through hole 34 from the distal side and fixed to the through hole 34. A structure for fixing the disk portion 30 to the main shaft 21 and the distal shaft 24 is not particularly limited. In addition, the disk portion 30 may be formed integrally with the distal shaft 24. The outer surface 33 is contactable with an inner peripheral surface of the tubular member 110. The outer surface 33 may be fitted to the inner peripheral surface of the tubular member 110 with a friction to an extent so as not to slide unless the operator applies a force, and so as to slide when the operator applies a force. Alternatively, the outer surface 33 may have a clearance such that the outer surface 33 can freely slide with respect to the inner peripheral surface of the tubular member 110.

A thickness of the disk portion 30 (a distance between the distal surface 31 and the proximal surface 32) can be substantially constant, but may be different at different portions. For example, the thickness of the disk portion 30 may decrease radially outward. Accordingly, light incident from an inner wall surface of the through hole 34 into a material for the disk portion 30 can be propagated radially outward through the material while being reflected by a surface of the material.

A constituent material for the disk portion 30 is not particularly limited as long as the constituent material has a certain degree of rigidity and can transmit light having a wavelength emitted from the irradiation unit 50, and can be, for example, silicone, polyamide, polymethyl methacrylate, polyethylene terephthalate, polycarbonate, polytetrafluoroethylene, urethane, and combinations of the constituent materials. A maximum outer diameter of the disk portion 30 is not particularly limited, and can be, for example, 10 mm to 50 mm. A length of the disk portion 30 in the axial center direction is not particularly limited, and can be, for example, 5 mm to 60 mm.

Figure 7A:
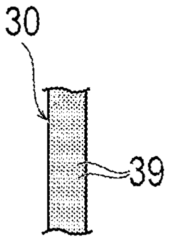
Figure 7B:
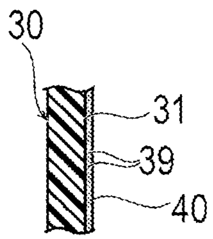
Figure 7C:
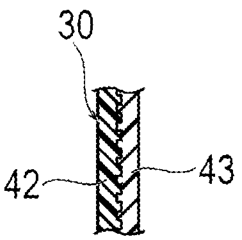

The disk portion 30 may have a structure that scatters light. Accordingly, the disk portion 30 emits light by the light received from the irradiation unit 50. Therefore, the treatment apparatus 10 can emit light to a relatively wide range through the disk portion 30 even in a range that cannot be directly irradiated with the light from the irradiation unit 50. For example, as in a fourth modification illustrated in FIG. 7A, the disk portion 30 may contain scatterers 39 inside the material. The scatterers 39 may be known materials, and may be fine particles of titanium oxide, styrene, silicone, or the like. As in a fifth modification illustrated in FIG. 7B, the disk portion 30 may include, on the distal surface 31, a scatterer coat 40 including the scatterer 39. The scatterer coat 40 is coated by mixing the scatterer 39 with a coat substrate having a refractive index different from that of the scatterer 39. The scatterer coat 40 may be formed on the proximal surface 32, or may be formed on both the distal surface 31 and the proximal surface 32. As in a sixth modification illustrated in FIG. 7C, the disk portion 30 may have a structure in which a first layer 42 and a second layer 43 having different refractive indexes are joined by a surface having irregularities. The disk portion 30 may include multiple minute irregular portions on the distal surface 31 and the proximal surface 32. The disk portion 30 may have a structure that reflects light.

The disk portion 30 may be formed in various shapes. It is preferable that the disk portion 30 is appropriately selectable according to a shape of the uterine vagina UV, the vaginal vault VF, or the vagina V of the patient.

Figure 8A:
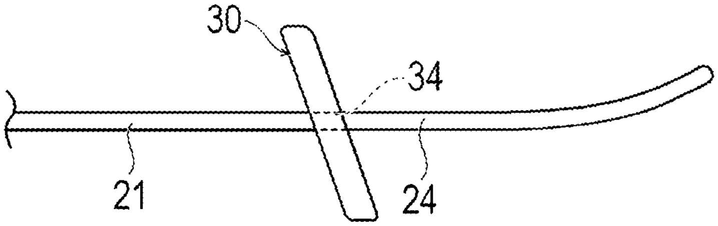

As in a seventh modification illustrated in FIG. 8A, the distal surface 31 and the proximal surface 32 of the disk portion 30 may be inclined with respect to a plane perpendicular to the axial center of the main shaft 21 (an axial center of the through hole 34). Accordingly, for example, light emitted from the distal surface 31 can be effectively emitted to a surface of the uterine vagina UV inclined with respect to the vagina V.

Figure 8B:
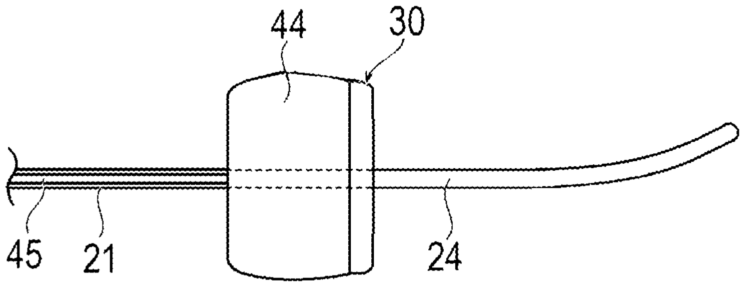

As in an eighth modification illustrated in FIG. 8B, the disk portion 30 may include a balloon 44 (a fixing portion). The balloon 44 can be disposed on a proximal surface 32 side of the disk portion 30, but may also be disposed on an outer surface 33 side of the disk portion 30. Alternatively, the entire disk portion 30 may be formed by the balloon 44. The balloon 44 can be inflated by being supplied with a fluid via a supply tube 45 extending from the first operation portion 60. The balloon 44 adheres to the inner peripheral surface of the tubular member 110 by being inflated. Accordingly, the irradiation device 20 can be fixed to the tubular device 100.

Figure 9A:
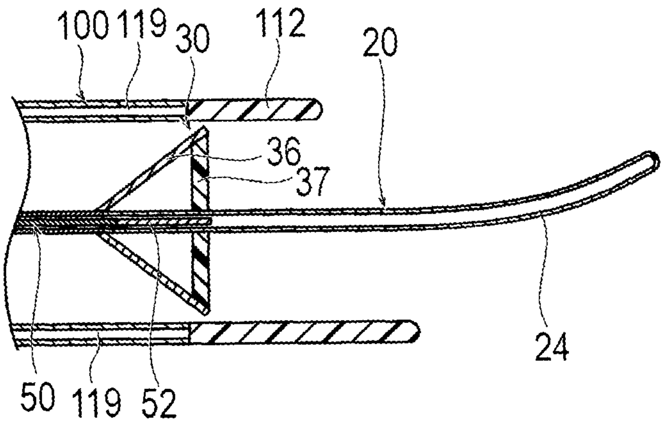

As in a ninth modification illustrated in FIG. 9A, the tubular device 100 may be formed with an optical waveguide 119 (a second irradiation unit). The optical waveguide 119 is disposed from a proximal end of the tubular device 100 to a tubular distal portion 112 provided at a distal portion of the tubular device 100. The tubular distal portion 112, which will be described in detail later, may have a structure that diffuses or scatters light. The disk portion 30 of the irradiation device 20 can include a disk-shaped disk member 37 having a structure for diffusing or scattering light, and a reflection member 36 extending from an outer peripheral surface of the disk member 37 toward the proximal side. The reflection member 36 has an outer peripheral surface and an inner peripheral surface whose diameters decrease in a tapered shape from the outer peripheral surface of the disk member 37 toward the proximal side. A length of the disk portion 30 including the reflection member 36 and the disk member 37 in the axial center direction (a longitudinal direction) is not limited, and is preferably equal to or longer than a length of a light-emitting unit 52 serving as a light emitting portion of the irradiation unit 50, which will be described later, in the axial center direction. Accordingly, light emitted from the light-emitting unit 52 disposed inside the disk portion 30 can be input to the disk portion 30 with a relatively small loss. The light emitted from the light-emitting unit 52 is input to the disk portion 30, reflected by the reflection member 36, and diffused by the disk member 37. The light-emitting unit 52 emits light inside the disk portion 30, and the excitation light emitted from the disk portion 30 is emitted only in the distal direction (a direction in which the external uterine ostium O and the uterine vagina UV are present with respect to the disk portion 30). Therefore, a treatment effect on the external uterine ostium O and the uterine vagina UV can be improved. A structure of the optical waveguide 119 (the second irradiation unit) is not particularly limited as long as the optical waveguide 119 can propagate light, and may be an optical fiber.

Figure 9B:
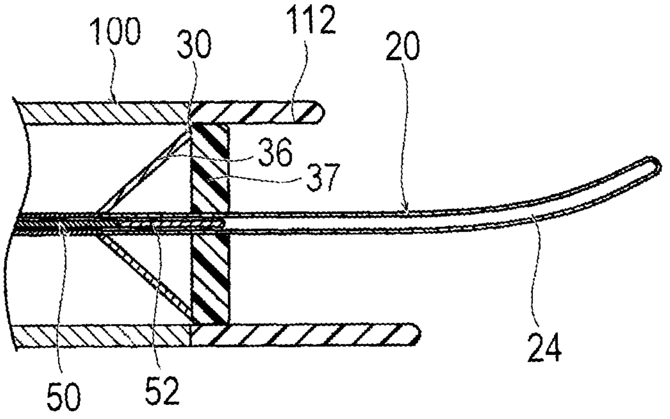

As in a 10th modification illustrated in FIG. 9B, the disk portion 30 includes the disk-shaped disk member 37 having a structure for diffusing or scattering light, and the reflection member 36 extending from a proximal surface on a radially outer side of the disk member 37 toward the proximal side. The outer peripheral surface of the disk member 37 can come into contact with an inner peripheral surface of the tubular distal portion 112 provided at the distal portion of the tubular device 100. The reflection member 36 has an outer peripheral surface and an inner peripheral surface whose diameters decrease in a tapered shape from positions on the radially outer side of the proximal surface of the disk member 37 toward the proximal side. A length of the disk portion 30 including the reflection member 36 and the disk member 37 in the axial center direction is not limited, and is preferably equal to or longer than the length of the light-emitting unit 52 serving as the light emitting portion of the irradiation unit 50, which will be described later, in the axial center direction. Accordingly, the light emitted from the light-emitting unit 52 disposed inside the disk portion 30 can be input to the disk portion 30 with a relatively small loss. The light emitted from the light-emitting unit 52 at a position close to the proximal side than the disk member 37 is reflected by the reflection member 36, and diffused by the disk member 37. The light emitted from the light-emitting unit 52 inside the disk member 37 enters a material for the disk member 37 and is propagated to the inner peripheral surface of the tubular distal portion 112 of the tubular device 100. In order to facilitate propagating light from the outer peripheral surface of the disk member 37 to the inner peripheral surface of the tubular distal portion 112, it is preferable that portions of the disk member 37 which come into contact with the tubular distal portion 112 are transparent or have a structure that propagates light with a relatively small loss. The light propagated to the tubular distal portion 112 can be diffused or scattered by the tubular distal portion 112 and can be emitted in the distal direction or in a direction substantially perpendicular to an axial center direction of the tubular device 100.

As illustrated in FIGS. 1 and 4, the irradiation unit 50 is elongated, and includes at least one optical fiber 51 that propagates light. The irradiation unit 50 includes, at a distal portion of the irradiation unit 50, the light-emitting unit 52 that emits light outward. A proximal portion of the irradiation unit 50 is connectable to the light output device 80 which outputs light. The irradiation unit 50 can receive near-infrared rays from the light output device 80, propagate the near-infrared rays to the light-emitting unit 52, and emit the near-infrared rays from the light-emitting unit 52. The irradiation unit 50 may be formed by an optical waveguide other than the optical fiber. The irradiation unit 50 is inserted into the irradiation lumen 25 from the insertion port 28. The irradiation unit 50 is movable in the axial center direction in the irradiation lumen 25 and is rotatable. The irradiation unit 50 may be immovable and non-rotatable in the irradiation lumen 25.

Figure 10A:
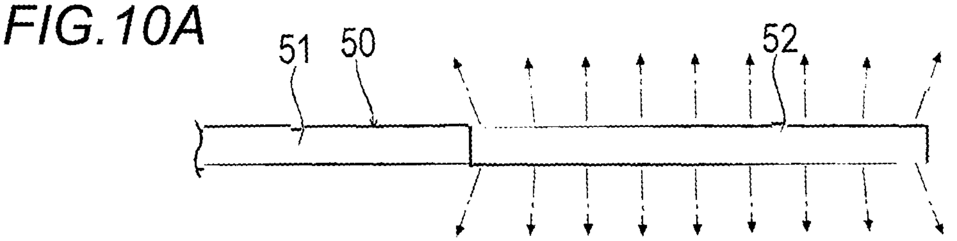
Figure 10B:
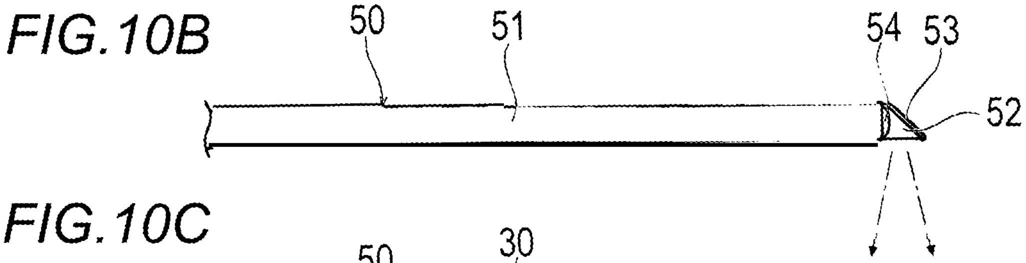

As illustrated in FIGS. 4 and 10A, the light-emitting unit 52 can be a cylindrical diffuser that is connected to a cut end of the optical fiber 51 and diffuses or scatters light received from the optical fiber 51. The diffuser may be formed integrally with the optical fiber 51 by processing a surface or an inside of the optical fiber 51, or may be the cut end of the optical fiber 51. In this case, it is preferable to provide a plurality of optical fibers 51 to emit light with a wide irradiation angle. As in an 11th modification illustrated in FIG. 10B, the light-emitting unit 52 may be formed by a mirror 53 and/or a lens 54 disposed at the cut end of the optical fiber 51. By forming the light-emitting unit 52 by the mirror 53 and/or the lens 54, the irradiation angle of light can be widened. By rotating the optical fiber 51 inside the irradiation lumen 25, the light-emitting unit 52 can emit light in a relatively wider range.

Figure 10C:
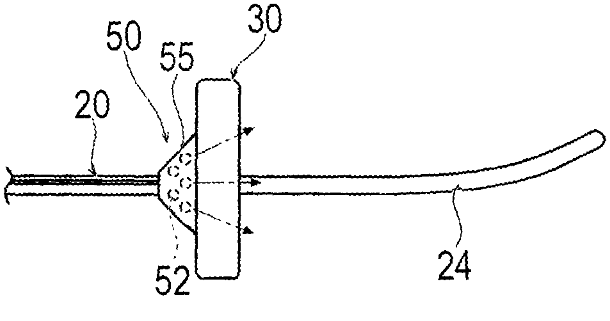

As a method for propagating light to the disk portion 30, the light-emitting unit 52 may not be disposed inside the main shaft 21 or the distal shaft 24. For example, as in a 12th modification illustrated in FIG. 10C, the irradiation unit 50 may include an irradiation auxiliary unit 55 that surrounds the main shaft 21 on a proximal side of the disk portion 30, and the light-emitting unit 52 may be disposed in the irradiation auxiliary unit 55. The irradiation auxiliary unit 55 has an inner peripheral surface that expands toward the distal direction in a manner of covering a part of a surface of the disk portion 30 on the proximal side. The light-emitting unit 52 is disposed on the inner peripheral surface. The light-emitting unit 52 can be, for example, the end of the optical fiber, the diffuser, the mirror, the lens, and a light-emitting diode (LED) that emits light by electric power. When the light-emitting unit 52 of the irradiation auxiliary unit 55 emits light, light is emitted from the proximal side of the disk portion 30 to the inside of the disk portion 30. Accordingly, the disk portion 30 can emit light substantially as a whole by receiving light from the light-emitting unit 52 of the irradiation auxiliary unit 55. The light-emitting unit 52 provided in the irradiation auxiliary unit 55 may be used together with the irradiation unit 50 provided in the irradiation lumen 25.

The first operation portion 60 is a portion to be held by the operator to operate the irradiation device 20, as illustrated in FIGS. 1 and 3. The first operation portion 60 includes a first operation portion main body 61 to which the proximal portion of the main shaft 21 is fixed, and a first fixing portion 62 for fixing the tubular device 100. The insertion port 28, which is an inlet of the irradiation lumen 25, is disposed at a proximal portion of the first operation portion main body 61. The first fixing portion 62 can include, for example, a plurality of convex portions on which a second fixing portion 123 provided in the tubular device 100 can be hooked. The first fixing portion 62 is preferably capable of fixing the second fixing portion 123 at any position.

As illustrated in FIGS. 1, 3, and 4, the tubular device 100 can include the tubular member 110 and a second operation portion 120. The tubular member 110 can include a tubular proximal portion 111 and the tubular distal portion 112. The tubular device 100 is used with the irradiation device 20 inserted into the tubular member 110.

The tubular proximal portion 111 can be a circular tube, and the second operation portion 120 is fixed to a proximal portion of the tubular proximal portion 111. The tubular proximal portion 111 is formed of a transparent material to ensure a visual field of the operator. Scale marks 115 arranged in the axial center direction are attached to an outer peripheral surface of the tubular proximal portion 111. The scale marks 115 can be used to check a depth of insertion of the tubular proximal portion 111 into the irradiation device 20 or a living body such as the vagina V. A constituent material for the tubular proximal portion 111 is not particularly limited as long as the constituent is transparent, and can be, for example, silicone, polyamide, polymethyl methacrylate, polyethylene terephthalate, polycarbonate, polytetrafluoroethylene, urethane, and combinations of the constituent materials listed.

The tubular distal portion 112 is a circular tube disposed on a distal side of the tubular proximal portion 111. The tubular distal portion 112 is formed of a transparent or translucent material capable of transmitting light having a wavelength emitted by the irradiation unit 50. A constituent material for the tubular distal portion 112 is not particularly limited, and can be, for example, silicone, polyamide, polymethyl methacrylate, polyethylene terephthalate, polycarbonate, polytetrafluoroethylene, urethane, and combinations of the constituent materials listed. The tubular distal portion 112 has a structure that diffuses or scatters light. Therefore, similarly to the disk portion 30, the tubular distal portion 112 may contain scatterers in at least a part of the constituent material, may have multiple irregularities formed on an inner surface or an outer surface of the tubular distal portion 112, or may have a multi-layer structure in which materials having different refractive indexes are joined by a surface on which multiple irregularities are formed. A most distal end of the tubular distal portion 112 is inclined with respect to a plane perpendicular to an axial center. Therefore, the tubular distal portion 112 is formed with a protruding portion 113 that protrudes most in the distal direction at a part of the tubular distal portion 112 in a peripheral direction. The tubular distal portion 112 can be formed with a depression portion 114 having a smallest protruding amount in the distal direction on an opposite side of the protruding portion 113 in the peripheral direction. By disposing the depression portion 114 on an anterior vaginal vault AV side near a vaginal introitus and disposing the protruding portion 113, which is on an opposite side of the depression portion 114, on a posterior vaginal vault RV side far from the vaginal introitus, the distal portion of the tubular member 110 can be brought relatively close to the entire vaginal vault VF including the anterior vaginal vault AV and the posterior vaginal vault RV. Therefore, light can be effectively emitted to a range where light is difficult to reach, including the posterior vaginal vault RV and the anterior vaginal vault AV. An outer diameter of the tubular member 110 can be, for example, 20 mm to 60 mm.

The tubular member 110 may be formed in various shapes. It is preferable that the tubular member 110 is appropriately selectable according to the shape of the uterine vagina UV, the vaginal vault VF, or the vagina V of the patient.

Figure 11A:
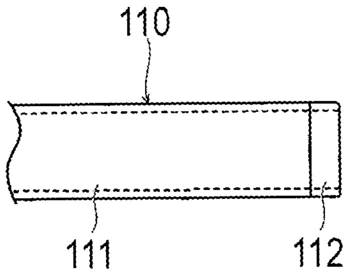

As in a 13th modification illustrated in FIG. 11A, the most distal end of the tubular member 110 may be perpendicular to an axial center of the tubular member 110. As in a 14th modification illustrated in FIG. 11B, the tubular member 110 may include a balloon 115 (a fixing portion) in the tubular member 110. The balloon can be inflated by being supplied with a fluid via a supply tube 116 extending from the second operation portion 120. By being inflated, the balloon adheres to the disk portion 30 disposed inside the tubular member 110. Accordingly, the irradiation device 20 can be fixed to the tubular device 100.

Figure 11B:
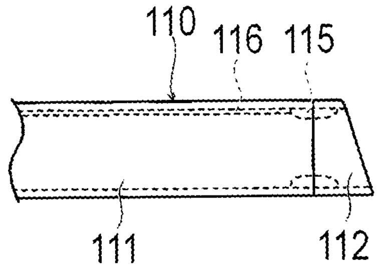
Figure 11C:
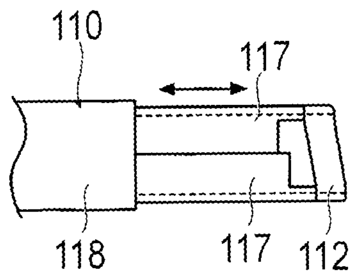

As in a 15th modification illustrated in FIG. 11C, the tubular proximal portion 111 may be halved into two half members 117. The two half members 117 are slidable in the axial center direction. The two half members 117 are accommodated in, for example, an outer tube 118 which is a tubular body such that the two half members 117 are not separated from each other. One half member 117 is fixed to the outer tube 118, and the other half member 117 is slidable with respect to the outer tube 118. The tubular distal portion 112 is fixed at positions of distal portions of the respective half members 117, the positions being separated from each other. The tubular distal portion 112 can be formed of a flexibly deformable material. Accordingly, by sliding the two half members 117, an inclination degree of the most distal end of the tubular distal portion 112 can be freely changed. Therefore, the operator can freely adjust the shape of the tubular member 110 according to the shape of the uterine vagina UV, the vaginal vault VF, or the vagina V of the patient.

The second operation portion 120 is a portion to be held by the operator to operate the tubular device 100, as illustrated in FIGS. 1 and 3. The second operation portion 120 can include a second operation portion main body 121 that is to be held by the operator for operation, a support portion 122 for supporting the irradiation device 20, and the second fixing portion 123 for fixing the irradiation device 20. The second operation portion main body 121 is fixed to an outer peripheral surface of the tubular member 110 at a proximal portion. The second operation portion main body 121 extends from the outer peripheral surface of the tubular member 110 at the proximal portion toward the proximal side and extends outward in a radial direction of the tubular member 110. The support portion 122 and the second fixing portion 123 are connected to the second operation portion main body 121. The support portion 122 is a portion that holds the proximal portion of the main shaft 21 at an appropriate position. The support portion 122 can be formed, for example, by branching into two to be able to sandwich and hold the main shaft 21. The second fixing portion 123 can be, for example, an arch-shaped member capable of rotating with respect to the second operation portion main body 121 and being hooked on the convex portion of the first fixing portion 62 provided in the irradiation device 20.

The light output device 80 can output light having any wavelength to the optical fiber 51 of the irradiation unit 50 with any intensity (power) or energy. The light output device 80 outputs near-infrared rays having a wavelength of, for example, 660 nm to 740 nm, to the optical fiber 51 such that light can be emitted at an intensity (power) of, for example, 1 mW to 5 W, and an energy of, for example, 1 Jcm-2 to 50 Jcm-2.

Next, the treatment method using the treatment apparatus 10 according to the embodiment will be described.

First, the antibody-photosensitive substance is administered intravenously. Approximately 12 hours to 36 hours after the intravenous administration, the operator inserts the tubular device 100, which is not combined with the irradiation device 20, from the vaginal introitus into the vagina V. The tubular member 110 passes through the vaginal introitus starting from the tubular distal portion 112 and is inserted into the vagina V. At this time, the second operation portion main body 121 of the tubular device 100 extends from the outer peripheral surface of the tubular member 110 at the proximal portion toward the proximal side and extends outward in the radial direction of the tubular member 110, and does not obstruct the visual field of the operator. The tubular member 110 is transparent and does not obstruct the visual field of the operator. Therefore, the operator can open the vaginal introitus by the tubular member 110 and rather easily insert the treatment apparatus 10 from the vaginal introitus into the vagina V. Therefore, this treatment method does not require a vaginal speculum. The vaginal introitus may also be opened by using a vaginal speculum.

Next, the operator inserts the irradiation device 20 into the tubular member 110 starting from a proximal side of the tubular member 110. At this time, the disk portion 30 of the irradiation device 20 is disposed inside the tubular member 110, but the first fixing portion 62 is not fixed to the second fixing portion 123. Therefore, the irradiation device 20 is movable with respect to the tubular device 100 along the axial center of the tubular member 110. Next, as illustrated in FIG. 12, the operator inserts the distal portion of the distal shaft 24 from the external uterine ostium O into the cervical canal CC while visually checking the distal portion of the distal shaft 24. At this time, since the tubular member 110 is transparent, the operator can rather easily insert the distal shaft 24 from the external uterine ostium O into the cervical canal CC by viewing the distal shaft 24. Since the irradiation device 20 is not fixed to the tubular device 100, the irradiation device 20 can be appropriately moved with respect to the tubular device 100. Therefore, the operator can rather easily position the distal shaft 24 at a desired position with respect to the cervical canal CC.

Next, as illustrated in FIG. 13, the operator pushes the tubular device 100, and presses the tubular member 110 toward the uterine vagina UV. Since the distal shaft 24 inserted into the cervical canal CC from the external uterine ostium O is connected to a center of the disk portion 30 disposed inside the tubular member 110, the distal shaft 24 is positioned substantially at a center of an opening portion of the tubular member 110 on a distal side. Therefore, the uterine vagina UV positioned around the external uterine ostium O rather easily enters a recessed portion that extends from the opening portion of the tubular member 110 on the distal side to the disk portion 30. Therefore, the tubular distal portion 112, which is positioned on a radially outer side of the disk portion 30 and protrudes in the distal direction, approaches the vaginal vault VF. At this time, the depression portion 114 of the tubular distal portion 112 can come into contact with or approach the anterior vaginal vault AV near the vaginal introitus. The protruding portion 113 of the tubular distal portion 112 can come into contact with or approach the posterior vaginal vault RV far from the vaginal introitus. If the tubular distal portion 112 is flexibly deformable, the tubular distal portion 112 can be deformed following the shape of the vaginal vault VF and abut against a wide range of the vaginal vault VF. At least a part of the ring-shaped tubular distal portion 112 preferably abuts against the vaginal vault VF. Accordingly, the tubular member 110 can be positioned with respect to the cervix U and the vagina V. The operator may move the distal shaft 24 together with the tubular member 110 when positioning the tubular member 110. In this case, the tubular member 110 and the distal shaft 24 are simultaneously positioned with respect to the cervix U and the vagina V.

Next, the operator fixes the irradiation device 20 and the tubular device 100. For this purpose, for example, the second fixing portion 123 is fixed to the first fixing portion 62. Alternatively, when the balloon 44 (the fixing portion) is disposed on the disk portion 30 as illustrated in FIG. 8B, the balloon 44 may be inflated to fix the irradiation device 20 and the tubular device 100. Alternatively, when the balloon 115 is disposed on the tubular member 110, as illustrated in FIG. 11B, the balloon 115 may be inflated to fix the irradiation device 20 and the tubular device 100.

Next, the operator disposes the light-emitting unit 52 of the irradiation unit 50 inside the distal shaft 24. At this time, the light-emitting unit 52 is disposed at a position where light can be emitted to the disk portion 30 and the tubular distal portion 112. Thereafter, the operator operates the light output device 80 to supply near-infrared rays to the irradiation unit 50.

Accordingly, the light-emitting unit 52 inside the distal shaft 24 can effectively emit the near-infrared rays to the tumor cells C positioned in the cervix U. When the distal shaft 24 has a function of diffusing or scattering light, the distal shaft 24 diffuses the near-infrared rays and emits light. An irradiation direction of the near-infrared rays from the light-emitting unit 52 includes a direction substantially perpendicular to an axial center of the distal shaft 24. Therefore, the light-emitting unit 52 can effectively emit the near-infrared rays from the cervical canal CC to the tumor cells C positioned in the cervix U. The tubular member 110 alone can also emit near-infrared rays (see FIG. 9A). In this case, a proximal end of the tubular member 110 is connected to a light source such as the light output device 80.

When the near-infrared rays are emitted from the cervical canal CC, the near-infrared rays reach the antibody-photosensitive substance accumulated in the tumor cells C in the cervix U. Accordingly, a chemical change occurs in the antibody-photosensitive substance that receives the near-infrared rays, which serve as the excitation light, and then the structural change occurs in the antibody-photosensitive substance, which generates holes in the cell membranes. Accordingly, the tumor cells C irradiated with the near-infrared rays are destroyed.

Since the disk portion 30 and the tubular distal portion 112, which receive light from the light-emitting unit 52, have a function of diffusing or scattering light, the entire disk portion 30 and tubular distal portion 112 emit light. That is, a part of the near-infrared rays that reaches the disk portion 30 and the tubular distal portion 112 is transmitted through the disk portion 30 and the tubular distal portion 112. A part of the near-infrared rays that reaches the disk portion 30 and the tubular distal portion 112 is scattered or diffused by the disk portion 30 and the tubular distal portion 112, and then emitted to a wide range. Therefore, the light-emitting unit 52, the disk portion 30, and the tubular distal portion 112 can effectively emit the near-infrared rays to the tumor cells C positioned mainly at the external uterine ostium O, the uterine vagina UV, the vaginal vault VF, and the site or location that is near the vaginal vault VF and is on the vaginal introitus side relative to the vaginal vault VF of the vagina V. Multiple folds are present in a vaginal wall on the vaginal introitus side relative to the vaginal vault VF of the vagina V, and by disposing the tubular distal portion 112 near the vaginal vault VF, incident angles of the near-infrared rays to the vaginal wall become relatively small. Therefore, reflection of light can be reduced as much as possible, and the near-infrared rays can be effectively emitted to the tumor cells C.

When the near-infrared rays are emitted from an inside of the vagina V, the near-infrared rays reach the antibody-photosensitive substance accumulated in the tumor cells C mainly in the external uterine ostium O, the uterine vagina UV, the vaginal vault VF, and the site or location that is near the vaginal vault VF and is on the vaginal introitus side relative to the vaginal vault VF of the vagina V. Accordingly, the chemical change occurs in the antibody-photosensitive substance that receives the near-infrared rays, which serve as the excitation light, and then the structural change occurs in the antibody-photosensitive substance, which generates holes in the cell membranes. Accordingly, the tumor cells C irradiated with the near-infrared rays are destroyed.

The light-emitting unit 52 simultaneously emits the near-infrared rays from the inside of the cervical canal CC and the inside of the vagina V. The operator may cause the near-infrared rays to be emitted while moving the light-emitting unit 52 inside the irradiation lumen 25. Therefore, the operator can also cause the near-infrared rays to be emitted from the inside of the cervical canal CC and cause the near-infrared rays to be emitted from the inside of the vagina V separately. The operator may cause the near-infrared rays to be emitted while alternately moving the light-emitting unit 52 between the inside of the cervical canal CC and the inside of the vagina V.

As necessary, the operator can repeatedly perform treatment of emitting the near-infrared rays while moving the disk portion 30, the tubular member 110, and the irradiation unit 50 inside the vagina V and the cervical canal CC by moving the irradiation device 20 and the tubular device 100 as a whole. At this time, if the irradiation device 20 and the tubular device 100 are fixed to each other, the operation is relatively easy. Alternatively, the irradiation device 20 and the tubular device 100 may be separately operated by releasing the fixation of the irradiation device 20 and the tubular device 100. In this case, each of the irradiation device 20 and the tubular device 100 can be disposed at a desired position.

When the operator determines that the tumor cells C are sufficiently destroyed or a predetermined time passes, the operator stops emitting the near-infrared rays. Thereafter, the operator removes the second fixing portion 123 from the first fixing portion 62, and releases the fixation of the irradiation device 20 and the tubular device 100. Thereafter, the operator removes the irradiation device 20 out of the body and removes the tubular device 100 out of the body. The irradiation device 20 and the tubular device 100 may be simultaneously removed without releasing the fixation of the irradiation device 20 and the tubular device 100. Accordingly, this treatment method ends.

As described above, the treatment apparatus 10 according to the present embodiment is the treatment apparatus 10 configured to irradiate the antibody-photosensitive substance accumulated in the tumor cell C of cervical cancer with the excitation light. The treatment apparatus 10 can include: the tubular device 100 including the elongated tubular member 110; and the irradiation device 20 configured to be inserted into the tubular member 110. The irradiation device 20 includes the main shaft 21 including the distal portion and the proximal portion, the disk portion 30 disposed on a distal side of the main shaft 21, the distal shaft 24 protruding from the disk portion 30 toward the distal side, and the irradiation unit 50 disposed on the distal shaft 24 and configured to emit the excitation light.

According to the treatment apparatus 10 described above, the excitation light can be effectively emitted to the antibody-photosensitive substance accumulated in the tumor cells C in a relatively wide range including the cervix U in a state in which the distal shaft 24 is inserted into the cervical canal CC and the tubular member 110 is inserted into the vicinity of the vaginal vault VF. Therefore, this treatment apparatus 10 can improve a treatment effect of cancer in a range including at least a part of the cervix U.

The distal shaft 24 may be configured to emit the excitation light in the direction substantially perpendicular to the axial center of the distal shaft 24, and the disk portion 30 may be configured to emit the excitation light in a substantially distal direction. Accordingly, the excitation light can be emitted to the tumor cells C of the cervix U from both the distal shaft 24 and the disk portion 30, and thus the treatment effect can be improved.

The tubular member 110 may include the optical waveguide 119 (the second irradiation unit) configured to emit the excitation light in the direction substantially perpendicular to the axial center of the tubular member 110 and/or in the substantially distal direction. Accordingly, the excitation light can be emitted from both the irradiation unit 50 provided in the irradiation device 20 and the optical waveguide 119 (the second irradiation unit) provided in the tubular member 110 to the tumor cells C in the cervix U, and thus the treatment effect can be improved. Since the excitation light can be directly emitted from the optical waveguide 119 provided in the tubular member 110 to the tumor cells C in the vaginal vault VF, which is difficult for light to reach, the treatment effect can be improved.

The distal portion of the tubular member 110 may be configured to be deformed. Accordingly, the distal portion of the tubular member 110 can be deformed along the vaginal vault VF to be disposed in the vicinity of the vaginal vault VF. Therefore, the excitation light can be effectively emitted to the vicinity of the vaginal vault VF, which is difficult for light to reach, and the treatment effect can be improved.

The treatment apparatus 10 may further include the fixing portion configured to fix the irradiation device 20 to the tubular device 100. Accordingly, the irradiation device 20 and the tubular member 110 can be operated as one, and thus operability is improved. Since the irradiation device 20 can be maintained at an appropriate position with respect to the tubular member 110, the excitation light emitted from the irradiation device 20 can be appropriately propagated to the tubular member 110. Therefore, the excitation light emitted from the distal shaft 24, the disk portion 30, and the tubular member 110 can be appropriately emitted to the antibody-photosensitive substance.

The fixing portion may be the balloon 44 that is disposed on the disk portion 30 and configured to be inflated by inflowing a fluid in the balloon 44. Accordingly, by inflating the balloon 44 inside the tubular member 110, the irradiation device 20 can be rather easily and reliably fixed to the tubular member 110.

The fixing portion may be the balloon 115 that is disposed on the tubular member 110 and configured to be inflated by inflowing a fluid in the balloon 115. Accordingly, by inflating the balloon 115, the irradiation device 20 can be rather easily and reliably fixed to the tubular member 110.

An axial center of the disk portion 30 may be inclined with respect to the axial center of the main shaft 21, which facilitates disposing the disk portion 30 in accordance with an inclination of the uterine vagina UV with respect to the vagina V. Therefore, the excitation light emitted from the disk portion 30 can be appropriately emitted to the antibody-photosensitive substance.

The treatment method according to the present embodiment is a treatment method for cervical cancer. The treatment method includes: intravenously administering the antibody-photosensitive substance; inserting the tubular member 110 into the vagina V 12 to 36 hours after the intravenous administration; inserting the irradiation device 20 into the tubular member 110, the irradiation device 20 including the disk portion 30 configured to be disposed inside the tubular member 110, the distal shaft 24 protruding from the disk portion 30 toward the distal side, and the irradiation unit 50 configured to emit the excitation light of the antibody-photosensitive substance; inserting the distal shaft 24 into the cervical canal CC; and causing the irradiation unit 50 to emit light and emitting the excitation light from the disk portion 30, the distal shaft 24, and the tubular member 110 to a surrounding tissue.

According to the treatment method described above, the distal shaft 24 can be inserted from the external uterine ostium O into the cervical canal CC, and the tubular member 110 can be inserted up to the vaginal vault VF or near the vaginal vault VF, and thus by emitting the excitation light of the antibody-photosensitive substance from the distal shaft 24, the disk portion 30, and the tubular member 110, the excitation light can be effectively emitted to the antibody-photosensitive substance accumulated in the tumor cells C in a range including at least a part of the cervix U. Therefore, this treatment method can improve the treatment effect of cancer in a range including at least a part of the cervix U.

The treatment method further includes fixing a position of the irradiation device 20 to the tubular member 110. Accordingly, the irradiation device 20 and the tubular member 110 can be operated as one, and thus the operability can be improved. Since the irradiation device 20 can be maintained at an appropriate position with respect to the tubular member 110, light emitted from the irradiation device 20 can be appropriately propagated to the tubular member 110. Therefore, the excitation light emitted from the distal shaft 24, the disk portion 30, and the tubular member 110 can be appropriately emitted to the antibody-photosensitive substance.

The disclosure is not limited to the embodiments described above, and various modifications can be made by those skilled in the art within a scope of the technical idea of the disclosure.

Figure 14:
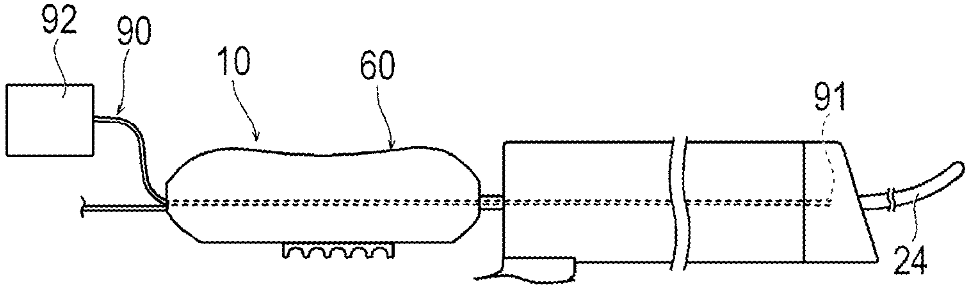
FIG. 14 is a plan view illustrating a treatment apparatus according to a 16th modification.

For example, as illustrated in FIG. 14, the treatment apparatus 10 may further include a detection unit 90 configured to detect fluorescence that is emitted by the antibody-photosensitive substance excited by being irradiated with near-infrared rays from the light-emitting unit 52 and has a wavelength (for example, 704 nm) different from a wavelength of irradiation light (for example, 689 nm). The detection unit 90 can include, for example, an optical waveguide 91 such as an optical fiber disposed in the irradiation lumen 25 like the irradiation unit 50 and receiving light, and an optical sensor 92 capable of detecting the amount of light. The detection unit 90 may include, at a position where the detection unit 90 receives light, a semiconductor sensor such as a complementary metal-oxide semiconductor (CMOS) image sensor that senses the light and converts the light into an electrical signal.

When the antibody-photosensitive substance accumulated in the tumor cells C is irradiated with the near-infrared rays, the antibody-photosensitive substance causes a photoreaction to emit the fluorescence, and destroys the tumor cells C. The antibody-photosensitive substance stops emitting the fluorescence after the tumor cells C are destroyed. Therefore, a degree of destruction of the tumor cells C due to emission of the excitation light can be checked by measuring a change in an intensity of the detected fluorescence by the optical sensor 92. Therefore, a progress state of the photoreaction for destroying the tumor cells C can be checked.

The detection unit 90 may be a device different from the treatment apparatus 10 including the irradiation unit 50 described above as long as the detection unit 90 can detect the fluorescence emitted by the antibody-photosensitive substance excited by receiving the near-infrared rays. The detection unit 90 may be inserted into the vagina V, a uterus, a rectum, a bladder, a urethra, an abdominal cavity, a blood vessel, a ureter, or the like to detect fluorescence. The detection of the fluorescence by the detection unit 90 may be performed in parallel with emission of the near-infrared rays by the treatment apparatus 10, or may be performed after the emission of the near-infrared rays by the treatment apparatus 10 is ended. The detection unit 90 may be inserted into the vagina V or the cervical canal CC after the treatment apparatus 10 is drawn out of the cervical canal CC and the vagina V. The detection unit 90 may detect fluorescence from a body surface outside a body in parallel with the emission of the near-infrared rays by the treatment apparatus 10 or after the emission of the near-infrared rays.

When the operator inserts the treatment apparatus 10 into the vagina V or the cervical canal CC, the detection unit 90 may be used to check a length of insertion of the treatment apparatus 10. For example, a position of the treatment apparatus 10 can be checked based on an image obtained from the CMOS image sensor or a change in the intensity or color of light obtained from the optical waveguide 91 such as an optical fiber.

In the tubular member 110, a reflection member may be interposed between the tubular proximal portion 111 and the tubular distal portion 112. The reflection member helps prevent the light emitted from the tubular distal portion 112 from being propagated to the tubular proximal portion 111, and thus the emission at the tubular distal portion 112 can be more efficiently performed.

In the tubular member 110, the constituent material for the tubular proximal portion 111 may not be a transparent material, and may be, for example, a metal material represented by stainless steel or the like. As a result, a wall thickness can be reduced while maintaining a rigidity of the tubular member 110, and the operability can be further improved.

The detailed description above describes embodiments of a treatment apparatus and a treatment method for cervical cancer. These disclosed embodiments represent examples of the treatment apparatus and the treatment method for cervical cancer disclosed here. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A treatment apparatus configured to irradiate an antibody-photosensitive substance accumulated in a tumor cell with excitation light, the treatment apparatus comprising:

a tubular device including an elongated tubular member;

an irradiation device configured to be inserted into the elongated tubular member;

wherein the irradiation device includes a main shaft including a distal portion and a proximal portion, a disk portion disposed on a distal side of the main shaft, a distal shaft protruding from the disk portion toward the distal side, and an irradiation unit disposed on the distal shaft and configured to emit the excitation light; and wherein the distal shaft is configured to emit the excitation light in a direction perpendicular to a central axis of the distal shaft, and the disk portion is configured to emit the excitation light in a distal direction.

2. The treatment apparatus according to claim 1, wherein the elongated tubular member includes a second irradiation unit configured to emit the excitation light in a direction perpendicular to a central axis of the elongated tubular member and/or in the distal direction.

3. The treatment apparatus according to claim 1, wherein a distal portion of the elongated tubular member is configured to be deformed.

4. The treatment apparatus according to claim 1, further comprising:

a fixing portion configured to fix the irradiation device to the tubular device.

5. The treatment apparatus according to claim 4, wherein the fixing portion is a balloon that is disposed on the disk portion and configured to be inflated by inflowing a fluid in the balloon.

6. The treatment apparatus according to claim 4, wherein the fixing portion is a balloon that is disposed on the elongated tubular member and configured to be inflated by inflowing a fluid in the balloon.

7. The treatment apparatus according to claim 1, wherein the disk portion includes a distal surface that is inclined with respect to the central axis of the main shaft.

8. The treatment apparatus according to claim 1, further comprising:

a detection unit configured to detect fluorescence emitted by the antibody-photosensitive substance.

9. A treatment apparatus configured to irradiate an antibody-photosensitive substance accumulated in a tumor cell with excitation light, the treatment apparatus comprising:

a tubular device including an elongated tubular member;

an irradiation device configured to be inserted into the elongated tubular member;

wherein the irradiation device includes a main shaft including a distal portion and a proximal portion, a disk portion disposed on a distal side of the main shaft, a distal shaft protruding from the disk portion toward the distal side, and an irradiation unit disposed on the distal shaft and configured to emit the excitation light; and wherein the disk portion includes a distal surface that is inclined with respect to a central axis of the main shaft.

10. A treatment apparatus configured to irradiate an antibody-photosensitive substance accumulated in a tumor cell with excitation light emitted from an irradiation unit, the treatment apparatus comprising:

a main shaft including a distal portion and a proximal portion;

a disk portion disposed on the distal portion of the main shaft, the disk portion extending from the main shaft in a radial direction of the main shaft so as to form an outer peripheral surface of the disk portion being apart from the main shaft and surrounding the main shaft;

a distal shaft protruding from the disk portion toward a distal direction;

wherein an irradiation lumen is continuously formed inside the main shaft and the distal shaft such that the irradiation unit is inserted in the irradiation lumen so as to be movable in an axial direction of the irradiation lumen;

wherein the distal shaft is configured to emit the excitation light toward an outside of the distal shaft when the irradiation unit is inserted in a lumen of the distal shaft that forms a portion of the irradiation lumen; and wherein the disk portion includes a distal surface and is configured to emit the excitation light toward an outside of the disk portion from the distal surface when the excitation light is input into the disk portion from the irradiation unit that is inserted in a lumen of the distal portion of the main shaft that forms a portion of the irradiation lumen.

11. The treatment apparatus according to claim 10, wherein the distal surface of the disk portion is inclined with respect to a central axis of the main shaft.

12. The treatment apparatus according to claim 10, further comprising:

an elongated tubular member; and wherein the disk portion is configured to be movably inserted, together with the main shaft and the distal shaft, into the elongated tubular member along a central axis of the elongated tubular member.

13. The treatment apparatus according to claim 12, wherein the outer peripheral surface of the disk portion is configured to come into contact with an inner peripheral surface of the elongated tubular member.

14. The treatment apparatus according to claim 13, wherein the outer peripheral surface of the disk portion is configured to be fitted to the inner peripheral surface of the elongated tubular member with a friction to an extent so as to slide when an operator applies to the disk portion a force exceeding the friction.

15. The treatment apparatus according to claim 13, wherein the outer peripheral surface of the disk portion is configured such that a clearance is defined between the outer peripheral surface of the disk portion and the inner peripheral surface of the elongated tubular member when the disk portion is inserted in the elongated tubular member.

16. The treatment apparatus according to claim 12, wherein the elongated tubular member includes a tubular distal portion that is configured to transmit the excitation light to an outside of the elongated tubular member; and wherein when the disk portion is disposed inside the tubular distal portion of the elongated tubular member proximal of a distal end portion of the tubular distal portion and the irradiation unit is inserted in the lumen of the distal portion of the main shaft, the disk portion transmits the excitation light emitted from the irradiation unit to the tubular distal portion while emitting the excitation light from the distal surface of the disk portion, and the tubular distal portion emits the excitation light an outside of the elongated tubular member from the distal end portion of the tubular distal portion disposed distal of the distal surface of the disk portion.

17. The treatment apparatus according to claim 12, wherein the elongated tubular member includes a tubular proximal portion with scale marks arranged along the central axis of the elongated tubular member.

18. The treatment apparatus according to claim 10, wherein the disk portion includes a structure that scatters the excitation light input into the disk portion.

19. The treatment apparatus according to claim 10, wherein the disk portion is configured to move with respect to the main shaft along a central axis of the main shaft.

20. The treatment apparatus according to claim 10, wherein the main shaft includes scale marks arranged on an outer peripheral surface of the main shaft along a central axis of the main shaft.

* * * * *